(12) United States Patent
Trovato et al.

(10) Patent No.: US 9,327,076 B2
(45) Date of Patent: May 3, 2016

(54) ELECTRONICALLY AND REMOTELY CONTROLLED PILL AND SYSTEM FOR DELIVERING AT LEAST ONE MEDICAMENT

(71) Applicant: Medimetrics Personalized Drug Delivery, Briarcliff Manor, NY (US)

(72) Inventors: Karen I Trovato, Putnam Valley, NY (US); Gerhard Spekowius, Roetgen (DE)

(73) Assignee: Medimetrics Personalized Drug Delivery, Eindhoven (NL)

( * ) Notice: Subject to any disclaimer, the term of this patent is extended or adjusted under 35 U.S.C. 154(b) by 0 days.

(21) Appl. No.: 14/010,090

(22) Filed: Aug. 26, 2013

(65) Prior Publication Data

US 2013/0345505 A1      Dec. 26, 2013

Related U.S. Application Data

(63) Continuation of application No. 11/574,200, filed as application No. PCT/IB2005/052771 on Aug. 24, 2005, now Pat. No. 8,518,022.

(60) Provisional application No. 60/605,364, filed on Aug. 27, 2004.

(51) Int. Cl.
*A61M 5/00* (2006.01)
*A61M 5/172* (2006.01)
(Continued)

(52) U.S. Cl.
CPC .............. *A61M 5/172* (2013.01); *A61B 5/411* (2013.01); *A61M 5/1723* (2013.01); *A61M 31/002* (2013.01); *A61B 5/073* (2013.01)

(58) Field of Classification Search
CPC . A61M 5/172; A61M 5/16827; A61M 31/00; A61K 9/20; A61B 1/041

USPC .......... 604/67, 151, 48, 500, 103.01
See application file for complete search history.

(56) References Cited

U.S. PATENT DOCUMENTS 4,564,363 A    1/1986  Bagnall et al.
4,572,403 A    2/1986  Benaroya
(Continued)

FOREIGN PATENT DOCUMENTS

CN       1958090       5/2007
CN       100998905 A   7/2007
(Continued)

OTHER PUBLICATIONS

Astaras, et al., "A Miniature Integrated Electronics Sensor Capsule for Real-Time Monitoring of the Gastrointestinal Tract (Ideas)", ICBME, 2002, 2 pages.

(Continued)

*Primary Examiner* — Aarti B Berdichevsky
(74) *Attorney, Agent, or Firm* — Lee & Hayes, PLLC

(57) ABSTRACT

An electronically and remotely controlled pill (500) or medicament delivery system is provided. The pill (500) includes a housing (102); a medicament reservoir (104) for storing a medicament; an electronically controlled release valve or hatch (106) for dispensing one or more medicaments stored in the medicament reservoir (104) while traversing the gastrointestinal tract; control and timing circuitry (108) for opening and closing the valve (106); and a battery (109). The control and timing circuitry (108) opens an closes the valve (106) throughout a dispensing time period in accordance with a preset dispensing timing pattern which is programmed within the control and timing circuitry (108). RF communication circuitry receives control signals for remotely overriding the preset dispensing timing pattern, reprogramming the control and timing circuitry (108) or terminating the dispensing of the medicament within the body. The pill (500) includes an RFID tag (508) for tracking, identification, inventory and other purposes.

27 Claims, 4 Drawing Sheets

(51) Int. Cl.
*A61B 5/00* (2006.01)
*A61M 31/00* (2006.01)
*A61B 5/07* (2006.01)

(56) References Cited

U.S. PATENT DOCUMENTS

| | | | |
|---|---|---|---|
| 4,814,180 A | 3/1989 | Eckenhoff et al. | |
| 5,071,040 A | 12/1991 | Laptewicz, Jr. | |
| 5,170,801 A | 12/1992 | Casper et al. | |
| 5,279,607 A | 1/1994 | Schentag et al. | |
| 5,318,557 A | 6/1994 | Gross | |
| 5,395,366 A * | 3/1995 | D'Andrea et al. | 604/890.1 |
| 5,423,779 A | 6/1995 | Yeh | |
| 5,567,592 A | 10/1996 | Benet et al. | |
| 5,853,386 A | 12/1998 | Davis et al. | |
| 6,053,899 A | 4/2000 | Slanda et al. | |
| 6,182,941 B1 | 2/2001 | Scheurenbrand et al. | |
| 6,423,779 B2 | 7/2002 | Sue et al. | |
| 6,632,216 B2 | 10/2003 | Houzego et al. | |
| 6,699,214 B2 | 3/2004 | Gellman | |
| 6,776,165 B2 | 8/2004 | Jin | |
| 6,800,060 B2 | 10/2004 | Marshall | |
| 6,803,373 B2 | 10/2004 | Schellens | |
| 6,929,636 B1 | 8/2005 | von Alten | |
| 7,014,640 B2 | 3/2006 | Kemppainen et al. | |
| 7,030,132 B2 | 4/2006 | Schellens et al. | |
| 7,282,045 B2 * | 10/2007 | Houzego et al. | 604/890.1 |
| 8,021,357 B2 | 9/2011 | Tanaka et al. | |
| 8,100,889 B2 | 1/2012 | Kawano et al. | |
| 8,308,681 B2 | 11/2012 | Slocum et al. | |
| 2002/0072735 A1 | 6/2002 | Kupperblatt et al. | |
| 2003/0020810 A1 | 1/2003 | Takizawa et al. | |
| 2003/0213495 A1 | 11/2003 | Fujita et al. | |
| 2004/0054278 A1 | 3/2004 | Kimchy et al. | |
| 2004/0242962 A1 * | 12/2004 | Uchiyama | 600/118 |
| 2004/0267240 A1 | 12/2004 | Gross et al. | |
| 2005/0147559 A1 | 7/2005 | von Alten | |
| 2005/0222537 A1 | 10/2005 | Dinsmoor et al. | |
| 2005/0234431 A1 | 10/2005 | Williams et al. | |
| 2006/0145876 A1 | 7/2006 | Kimura et al. | |
| 2006/0155174 A1 | 7/2006 | Glukhovsky et al. | |
| 2007/0138027 A1 | 6/2007 | Dinsmoor et al. | |
| 2007/0213659 A1 | 9/2007 | Trovato et al. | |
| 2007/0250045 A1 | 10/2007 | Trieu | |

FOREIGN PATENT DOCUMENTS

| | | |
|---|---|---|
| DE | 3317536 | 11/1984 |
| DE | 3339323 | 5/1985 |
| EP | 0257786 | 2/1988 |
| FR | 2591095 | 6/1987 |
| FR | 2794654 | 12/2000 |
| FR | 2835730 | 8/2003 |
| GB | 2374149 | 9/2002 |
| JP | 2001526939 | 12/2001 |
| JP | 2002532162 | 10/2002 |
| JP | 2003520108 | 7/2003 |
| JP | 2005536307 | 12/2005 |
| WO | WO9407562 | 4/1994 |
| WO | WO0152923 | 7/2001 |
| WO | WO03008637 | 1/2003 |
| WO | WO03068061 | 8/2003 |
| WO | WO2004066903 | 8/2004 |
| WO | WO2005025647 | 3/2005 |
| WO | WO2005038049 | 4/2005 |
| WO | WO2006021932 | 3/2006 |
| WO | WO2006025013 | 3/2006 |
| WO | WO2006037434 | 4/2006 |
| WO | WO2006044049 | 4/2006 |
| WO | WO2006056944 | 6/2006 |
| WO | WO2006077529 | 7/2006 |
| WO | WO2008029372 | 3/2008 |
| WO | WO2008038199 | 4/2008 |
| WO | WO2008062335 | 5/2008 |

OTHER PUBLICATIONS

Barge, et al., "Editorial: Improving the Health of Canadians", vol. 1, No. 2, Sep. 2003, 6 pages.
Translated Chinese Office Action mailed Jan. 15, 2013 for Chinese patent application No. 201080015953.5, a counterpart foreign application of U.S. Appl. No. 13/262,841, 17 pages.
Translated Chinese Office Action mailed Jan. 21, 2013 for Chinese patent application No. 201080040663.6, a counterpart foreign application of U.S. Appl. No. 13/390,111, 8 pages.
Translated Chinese Office Action mailed Mar. 14, 2013 for Chinese patent application No. 200980112018.8, a counterpart foreign application of U.S. Appl. No. 12/933,891, 12 pages.
The Chinese Office Action mailed May 13, 2013 for Chinese patent application No. 201080015284.1, a counterpart foreign application of U.S. Appl. No. 13/262,861, 11 pages.
Evans, et al., "Measurement of Gastrointestinal pH Profiles in Normal Ambulant Human Subjects", GUT, vol. 29, 1988, pp. 1035-1041.
Hanluain, Daithi, O., "Ultrasound to Aid Drug Delivery", Wired News, Mar. 13, 2002, 3 pages.
Translated Japanese Office Action mailed Apr. 16, 2013 for Japanese Patent Applicaiton No. 2011-514179, a counterpart foreign application of U.S. Appl. No. 12/992,305, 9 pages.
Translated Japanese Office Action mailed Apr. 23, 2013 for Japanese patent application No. 2012-524322, a counterpart foreign application of U.S. Appl. No. 13/390,111, 6 pages.
Translated Japanese Office Action mailed Apr. 30, 2013 for Japanese patent application No. 2010-546431, a counterpart foreign application of U.S. Appl. No. 12/867,888, 4 pages.
Knapp, Louise, "Diagnosis and Medicine in a Pill", Jul. 28, 2003, 3 pages.
Kompella, et al., "Delivery System for Penetration Enhancement of Peptide and Protein Drugs: Design Considerations", Advanced Drug Delivery Reviews, vol. 46, 2001, pp. 211-245.
Office action for U.S. Appl. No. 12/992,305, mailed on Jul. 16, 2013, Zou et al., "Device for Delivery of Powder Like Medication in a Humid Environment", 14 pages.
Non-Final Office Action for U.S. Appl. No. 11/720,242, mailed on Jul. 3, 2013, Gerardus Rudolph Langereis et al., "Electronically Controlled Pill and System Having at Least One Sensor for Delivering at Least One Medicament", 22 pages.
Office action for U.S. Appl. No. 11/574,200, mailed on Sep. 11, 2012, Karen I. Trovato, et al., "Electronically and Remotely Controlled Pill and System for Delivering at Least One Medicament", 18 pages.
Paine, et al., "Characterization of Interintestinal and Intraintestinal Variations in Human CYP3A-Dependent Metabolism", The Journal of Pharmacology and Experimental Therapeutics, vol. 283, No. 3, 1997, pp. 1552-1562.
"Pioneering the Next Generation of Drug Delivery and Biosensing", MicroChips, 2 pages.
Siccardi, et al., "Regulation of Intestinal Epithelial Function: A Link Between Opportunities for Macromolecular Drug Delivery and Inflammatory Bowel Disease", Advanced Drug Delivery Reviews, vol. 57, 2005, pp. 219-235.
"The Smart Pill Diagnostic System", SmartPill Diagnostics, Inc., Jan. 2004, 2 pages.
Trovato, Karen, I., "Given Imaging", Medical Market Clipping, Mar. 2004, 6 pages.
Tully, et al., Smart Pills Could Prove Sweet for Semiconductor Vendors, Gartner, Inc., 2003, 5 pages.
Webb, Carol Ezzell, "Chip Shots", IEEE Spectrum, Oct. 2004, pp. 49-53.
Wilding, et al., "Remote Controlled Capsules in Human Drug Absorption (HDA) Studies", Critical Reviews in Therapeutic Drug Carrier Systems, 20(6), 2003, pp. 405-431.
The European Office Action mailed Nov. 6, 2014 for European patent application No. 05775739.5, a counterpart foreign application of U.S. Appl. No. 11/574,200, 5 pages.

* cited by examiner

ELECTRONICALLY AND REMOTELY CONTROLLED PILL AND SYSTEM FOR DELIVERING AT LEAST ONE MEDICAMENT

The present application is a continuation of U.S. patent application Ser. No. 11/574,200 filed Feb. 23, 2007 which is incorporated by reference herein in its entirety.

The present invention relates generally to medication delivery systems. More particularly, it relates to an electronically controlled pill and system for delivering at least one medicament.

A medicament is generally administered as a pill or a liquid to be taken at least one time per day. A person may be required to take or be administered several medicaments each day during the same or different times. This requires that the person or his caregiver maintain a log or remember which medicaments to take or administer at different times during the day.

A medicament, such as aspirin, taken by the person generally traverses the gastrointestinal tract where it is absorbed for treating an ailment or condition. Objects typically pass through the GI tract in 20-40 hours. Several medicaments are available as time-release capsules for releasing portions of the medicament into the body at different times. Time-release capsules utilize chemical reactions between chemical substances in the gastrointestinal tract and the coating of the capsules for releasing the medicament. Food, particularly proteins and fats, and the GI chemistry affect the speed of the journey of medicaments through the stomach. As such, medicaments, including medicaments available as time-release capsules, do not an exact follow a particular dispensing or dissolving pattern while traveling through the GI tract.

For example, one person may have more than a "normal" amount of chemical substances in the gastrointestinal tract due to a condition, an earlier-administered medicament, etc. and therefore, cause the coating of the time-release capsule to react quicker than normal. Accordingly, the medicament is released by the time-release capsule at a faster rate than an intended rate. However, another person may have less than the "normal" amount of chemical substance in the gastrointestinal tract and cause the coating of the time-release capsule to react slower than normal, thereby releasing the medicament at a slower rate than the intended rate.

Further, as with traditional medicaments available in non-time-release form, time-release capsules require a person or caregiver maintain a log or remember which medicaments to take or administer at different times during the day. For example, some medicaments must be taken at bedtime, such as NSAIDS for rheumatoid arthritis, to produce fewer gastrointestinal complications, such as indigestion. Other medicaments, such as the anti-inflammatory corticosteroid medication predisone, can cause insomnia when taken in high doses, and are typically taken in the morning. Still, other medicaments, such as antihistamines, are typically taken in the evening to prepare for symptoms that often occur in the morning.

Additionally, with traditional medicaments available in non-time-release form and time-release form, if more than the proper dosage is taken, there is no method of terminating the additional absorption of the non-absorbed medicament by the body. As such, the person's stomach may need to be pumped or the person is given additional medicaments to counteract the over-dosage.

Finally, there does not exist any system for automatically controlling the administration of medicaments as a function of external data, such as weather condition, pollen reports, patient related values such as blood-pressure or blood-sugar level, etc.

The present invention provides an electronically controlled pill or medicament delivery system for delivering or dispensing a medicament according to a preset dispensing timing pattern while traversing through the gastrointestinal tract. The preset dispensing timing pattern is fixed and is not susceptible to a person's physiological processes and conditions, mood, earlier-administered medicaments, etc. The electronically controlled pill includes control and timing circuitry for controlling the opening and closing of a valve or hatch according to the preset dispensing timing pattern for dispensing a medicament stored within a medicament reservoir of the pill. The electronically controlled pill allows a person to take all pills substantially simultaneously, at say 7:00 am, so that no more pills are required for the day. Medication that does not fit into one electronically controlled pill can be coordinated with other electronically controlled pills for the full day's payload regimen.

According to the present invention, all of the medicaments required to be taken during a particular time period, for example, during 24-hour period, can be provided within one or more electronically controlled pills which can all be taken at the same time. The electronically controlled pills can have different dispensing timing patterns, so that a full day's coverage can be obtained. As such, the present invention also provides a treatment system for administering two or more medicaments at the same time via the one or more electronically controlled pills. Each pill has an independent, preset dispensing timing pattern in order to dispense its medicaments within the body according to a dispensing pattern. The dispensing pattern can be varied from person to person depending on each person's physical condition, age, gender, ailments, etc. Further, at a preset moment in time during the dispensing timing patterns, the electronically controlled pills present in the body may be programmed to stop dispensing medicament, in the expectation that a new set of pills will be taken. This prevents accidental overdose by having only the most recently taken pills dispensing medicament in the body.

The treatment system of present invention enables an individual to take all of his medicaments at substantially the same time, e.g., in the morning or in the evening, and not at different times during a particular time period (e.g., a 24-hour period). The treatment system of the present invention further enables a caregiver to administer once per day (i.e., once per a 24-hour period) all of the medicaments for each patient of a hospital or resident of a nursing home (or animals in a shelter or veterinary facility). The system of the present invention therefore avoids the need for a caregiver to wake up or otherwise disturb a patient or resident for the sole purpose of administering a medicament, or to track down a patient or resident who may be in a different part of the hospital or nursing home for the sole purpose of administering a medicament. The system of the present invention also reduces the overload required for inventorying, ordering, tracking and logging the medicaments.

Additionally, the present invention provides a remote-controlled mechanism for remotely controlling the pill. As such, one can remotely control the quantity of medicament dispensed, reprogram the pill for changing the preset dispensing timing pattern, etc. The pill can be remotely controlled using RF communication circuitry, a piezo-electric element, or other known remote control mechanisms.

Various embodiments of the present disclosure will be described herein below with reference to the figures wherein.

Figure 1:
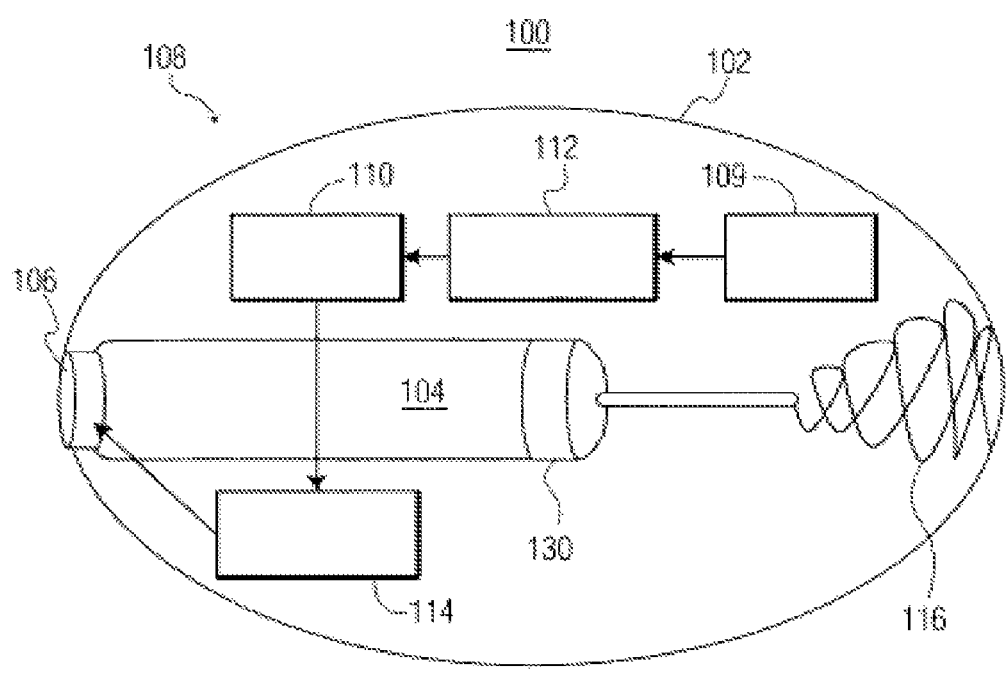
FIG. 1 is a schematic diagram of an electronically controlled pill in accordance with the present invention.

An electronically controlled pill or medicament delivery system according to the present invention is shown by FIG. 1, and further described with specificity hereinafter. The electronically controlled pill 100 is a self-contained, electronically controlled medicine delivery system. As described in detail below, the electronically controlled pill 100 includes programmed electronics that control a release mechanism according to a dispensing pattern for dispensing a medicament. The pill 100 is made from bio-compatibles materials such that the pill 100 is bio-compatible for at least the amount of time it requires to traverse the gastrointestinal tract. The bio-compatible materials are preferably stable in room temperature, such that the pill has a long shelf life. As used herein and in the claims the word "medicament" refers to medicines, non-medicinal substances, contrast agents, gases, fluids, liquids, chemicals, radiological agents, imaging markers, sensors for monitoring the person's vitals, etc.

The electronically controlled pill 100 includes an outer shell or housing 102; a medicament reservoir 104 for storing a medicament; an electronically controlled release valve or batch 106 for dispensing the medicaments stored in the medicament reservoir 104; control and timing circuitry 108 for opening and closing the valve 106; and a battery 109. The control and timing circuitry 108 opens and closes the valve 106 throughout a dispensing time period in accordance with a preset dispensing timing pattern as further described below. The preset dispensing timing pattern is pre-programmed and is not susceptible to a person's physiological processes and conditions, mood, earlier-administered medicaments, etc.

The shell 102 is preferably manufactured from materials used to fabricate implantable devices, including pacemaker leads and cardiac prostheses devices, such as artificial hearts, heart valves, intraaortic balloons, and ventricular assist devices. These materials include Pellethane® 2363 polyetherurethane series of materials available from Dow Chemical Company and Elasthane polyetherurethane available from the Polymer Technology Group, Inc. Other materials include PurSil® and CarboSil® also available from the Polymer Technology Group, Inc.

The amount that the valve 106 is opened at each moment in time (e.g., each second) of the dispensing time period is dependent upon the preset dispensing timing pattern which is programmed within timing circuitry 110 of the control and timing circuitry 108. The dispensing time period is defined as the time period from when the electronically controlled pill 100 is placed in a person's mouth to the time all of the medicament stored within the medicament reservoir 104 has been dispensed, or the day (24-hour period) has expired. This 24-hour period may be shifted slightly to account for differences in absorption in the stomach versus the colon.

Figure 2:
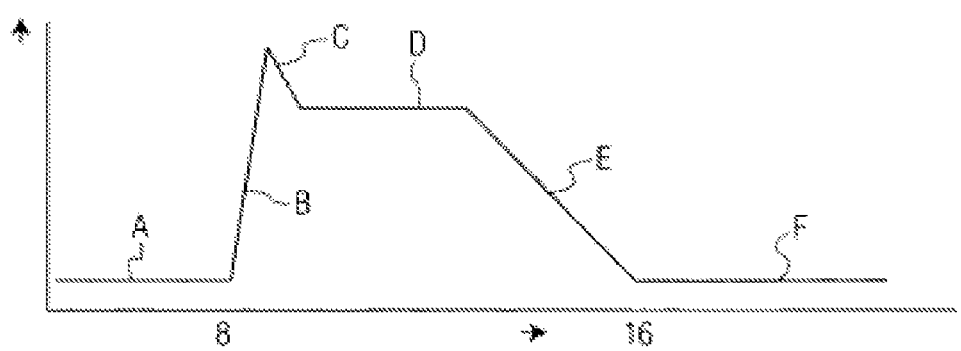
FIG. 2 is a chart illustrating an exemplary preset dispensing timing pattern for the electronically controlled pill in accordance with the present invention.

As shown by the exemplary preset dispensing timing pattern illustrated by FIG. 2, at dispensing time periods A, D and F, identical quantities of the medicament are dispensed throughout each of these dispensing time periods. Therefore, during these dispensing time periods, the valve 106 is kept open by the control and timing circuitry 108 to provide a fixed valve opening (or frequency of opening) for dispensing a predictable quantity of the medicament at each moment in time of dispensing time periods A, D and F. Approximately the same amount of medicament is dispensed at each moment in time during dispensing time periods A and F. During dispensing time period D, a higher quantity of medicament is dispensed than during dispensing time periods A and F.

However, at dispensing time periods B, C and E, as shown by FIG. 2, different quantities of the medicament are dispensed at each moment in time. Therefore, during dispensing time periods B, C and E, the valve opening is varied accordingly by the control and timing circuitry 108 to dispense a quantity of the medicament varying at each moment in time. During dispensing time period B, the quantity of medicament dispensed during each moment in time is increased compared to the previous moment in time; whereas during dispensing time periods C and E, the quantity of medicament dispensed during each moment in time is decreased compared to the previous moment in time.

In accordance with the present invention, during the entire dispensing time period, the control and timing circuitry 108 is programmed for closing the valve 106 and controlling the amount the valve 106 is opened for controlling the size of the valve opening or frequency of valve opening, such as is enabled by microfluidic systems of inkjet printers and the like. By controlling the size of the valve opening, the electronically controlled pill 100 can precisely control the quantity of medicament released during each moment in time (e.g., each second) of the dispensing time period.

By knowing the quantity or approximate quantity of medicament released during each moment in time by referring to a time release pattern, such as the one shown by FIG. 2, one can precisely determine the cumulative amount of medications released over a particular time period of the dispensing time period. For example, one can determine the cumulative amount of medicament released during the first six hours of the dispensing time period, the first two hours until the last hour of the dispensing time period, the entire dispensing time period, etc. One can also determine the amount of medicament dispensed during a particular moment of the dispensing time period, such as at two hours and fifteen minutes after the pill 100 has been administered.

The preset dispensing timing pattern may be varied from one electronically controlled pill 100 to another by programming the control and timing circuitry 108 of each pill 100 to have a different preset dispensing timing pattern. Therefore, two individuals can be administered the same medicament utilizing two different preset dispensing timing patterns. The timing patterns can be determined using a look-up table which correlates one or more characteristics of a person with one or more preset dispensing timing patterns.

For example, a look-up table can correlate at least one of age, gender, weight, etc. with preset dispensing timing patterns. The person would then be administered an electronic pill 100 which is programmed with one of the determined preset dispensing timing patterns. Accordingly, the pill 100 of the present invention enables the same medicament to be administered to different individuals using different dispensing timing patterns.

Additionally, for young and old people that have difficulty taking or remembering to take pills, the preset dispensing timing patterns are a way to reduce the number of pills taking during a particular time period, e.g., a 24-hour period. All of the medicament required to be administered during the particular time period to an individual can be provided in one pill 100 having a preset dispensing timing pattern for dispensing the medicament according to predetermined quantities during the particular time period. If the payload in one pill is insufficient, then two electronically controlled pills are used to dispense the same medicament, where one pill does not start dispensing the medicament until the other pill has dispensed its medicament, i.e., its dispensing time period has lapsed or ended. Further, the present invention reduces the amount of labor required to administer pills in places like hospitals, nursing homes and veterinary facilities. By reducing the number of times that pills are administered, the number of medicament administration errors can also be reduced.

With reference to FIG. 1, the control and timing circuitry 108 includes timing circuitry 110 programmed with the preset dispensing timing pattern, a start timer mechanism 112, a release controller 114 and a pressure mechanism 116. The start timer mechanism 112 enables activation of the timing circuitry 110. The battery 109 powers the control and timing circuitry 108 in order for each of the electromechanical components to operate during the dispensing time period.

In a preferred embodiment, the start timer mechanism 112 is a micro-electromechanical (MEM) mechanism having a sensor 118 for sensing the presence of a liquid, such as water, saliva, etc. When the pill 100 is taken or administered, the sensor 118 senses the presence of a liquid, and transmits an electrical signal to the timing circuitry 110. In an alternate embodiment the start timer mechanism is a button which is pushed to transmit the electrical signal to the timing circuitry 110. The button is pushed just before the pill 100 is administered to a person or animal.

In another embodiment, this can be achieved by dissolving a thin, water soluble coating that separates two electrical contacts, enabling the switch to close the circuit. In still another embodiment, the switch is manually triggered by the patient or caregiver.

Upon receiving the electrical signal, the timing circuitry 110 begins to clock the dispensing time period and control the release controller 114 by transmitting a signal thereto. The timing circuitry 110 includes a microprocessor programmed with the preset dispensing timing pattern for relaying the signal to the release controller 114, such that the medicament is dispensed during the dispensing time period substantially according to the preset dispensing timing pattern, such as the one shown by FIG. 2.

The voltage level of the signal relays the size of the valve opening for controlling the quantity of the medicament dispensed at each moment of the dispensing time period substantially according to the preset dispensing timing pattern as shown by FIG. 2. In an alternate embodiment, the signal transmitted by the timing circuitry 110 to the release controller 114 only relays the opening an closing of the valve 106 and not the size of the valve opening.

The release controller 114 is preferably a micro-electromechanical mechanism capable of receiving the signal from the timing circuitry and generating a signal having a variable voltage level to the electronically controlled valve 106 for closing the valve 106 and controlling the size of the valve opening or degree of opening of the valve 106 (in accordance with the voltage level of the received signal). In the simplest case, the release controller 114 is a transistor or D/A circuit that provides voltages to the valve 106 causing it to open or close.

The electronically controlled valve 106 is preferably a micro-electromechanical mechanism capable of being electrically controlled by a signal having a variable voltage levels. Each voltage level corresponds to a different size opening for the valve opening and one voltage level (or no voltage at all, i.e., no signal) corresponds to the valve 106 being closed. The valve 106 is similar in operation to valves used in ink-jet printers for dispensing ink in accordance with the amount that the valve is opened. The valve 106 is characterized as a microfluidic valve for controlling the movement of minute amount of liquids or gases in a miniaturized system.

In an alternate embodiment, the reservoir 104 is a micro-syringe, whereby pressure applied to a plunger of the syringe dispenses the medicament via a needle tip of the micro-syringe which is in fluid communication with an opening in the shell 102. In this embodiment, the opening replaces the valve 106. It is contemplated, however, that a check valve is placed at the needle tip of the micro-syringe to avoid leakage of the medicament during time periods within the dispensing time period where there should be no dispensing according to the preset dispensing timing pattern, and/or for controlling the quantity of medicament dispensed during the dispensing time period.

Figure 3:
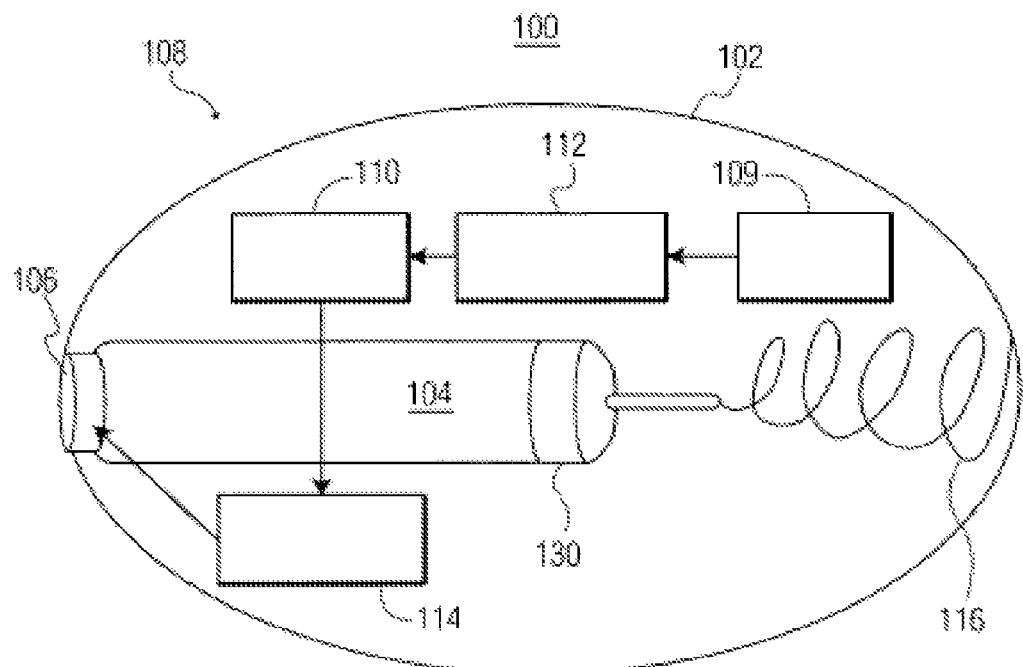
FIG. 3 is a schematic diagram of the electronically controlled pill dispensing a medicament in accordance with the present invention.

The pressure mechanism 116 is located outside the medicament reservoir 104 ensuring that the medicament is directed toward the valve 106. In the simplest case, the pressure mechanism 116 is preferably a biodegradable spring as shown by FIGS. 1 and 3. The pressure mechanism 116 can also be another type of spring, a piston, or any mechanism for performing the function of the pressure mechanism 116. That is, for performing the function of applying pressure to a piston-type member 130 when the valve 106 is open to push the piston-type member 130 towards the valve 106. As the piston-type member 130 moves towards the valve 106 pressure within the reservoir 104 causes the medicament to be dispensed as shown by FIG. 3.

In an alternate embodiment, the medicament reservoir 104 is kept under pressure to assure a proper quantity of medicament is dispensed in accordance with the degree of openness of the valve 106, without the need for the pressure mechanism 116. The pressure can be monitored by a pressure sensor which relays the monitored pressure to the control and timing circuitry 108. If the pressure is outside a predetermined range, the circuitry 108 can then adjust the valve opening to increase or decrease the pressure. Naturally, the pressure of the reservoir 104 can be different for each medicament and can depend on the medicament's viscosity.

It is contemplated that a look-up table or other data structure can be assessed by the circuitry 108 which correlates pressure, degree of valve opening, and other parameters, such as period of time in the dispensing time period, for determining, for example, the degree of valve opening by knowing the pressure, and vice versa. Based on the information obtained by assessing the look-up table, the circuitry 108 can then adjust the pressure, the valve opening, etc. These adjustments can be made in order to substantially track the preset dispensing timing pattern programmed within the pill 100.

According to the present invention, all of the medicaments required to be taken during a particular time period, for example, during a 24-hour period, can be provided within one or more electronically controlled pills 100 which can all be taken at the same time. As such, a treatment system of the present invention provides for two or more medicaments to be administered at the same time via the one or more electronically controlled pills 100. Each pill 100 has an independent, preset dispensing timing pattern in order to dispense its medicaments within the body according to a dispensing pattern. The dispensing pattern can be varied from person to person depending on each person's physical condition, age, gender, ailments, etc.

The treatment system of the present invention enables an individual to take all of his medicaments at substantially the same time, e.g., in the morning or in the evening, and not at different times during a particular time period (e.g., a 24-hour period). The treatment systems of the present invention further enables a caregiver to administer once per day (i.e., once per a 24-hour period) all of the medicaments for each patient of a hospital or resident of a nursing home (or animals in a shelter or veterinary facility). The system of the present invention therefore avoids the need for a caregiver to wake up or otherwise disturb a patient or resident for the sole purpose of administering a medicament, or to track down a patient or resident who may be in a different part of the hospital or nursing home for the sole purpose of administering a medicament.

Figure 4:
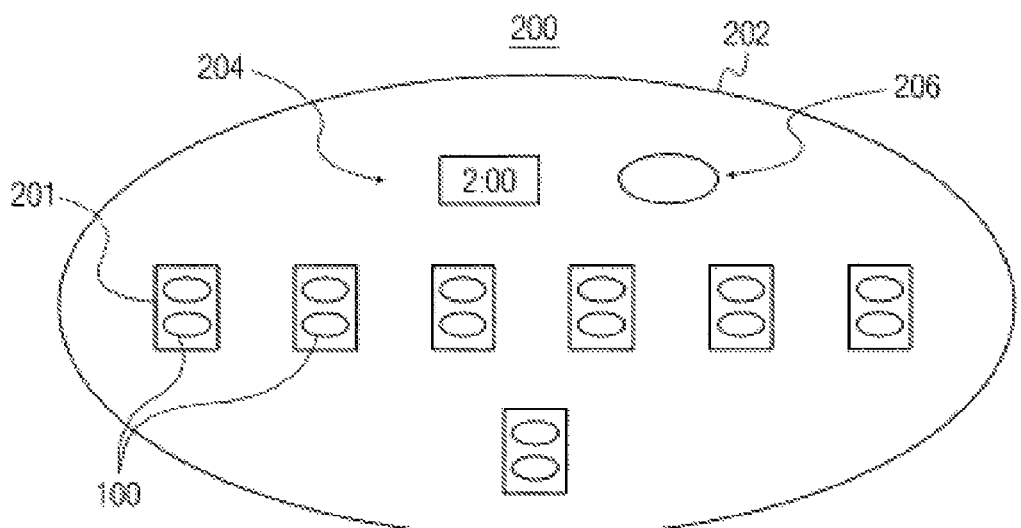
FIG. 4 is a diagram of a kit having a plurality of electronically controlled pills tailored for administration to a particular individual.

The present invention also provides a kit 200 as shown by FIG. 4 having two or more electronically controlled pills 100 packaged within a container 202. Each pill 100 is placed within an indenture or recess 201 of the container 202 and each pill 100 has an independent, preset dispensing timing pattern programmed therein. The pills 100 of the kit 200 are custom tailored for an individual (or animal), such that the individual or his caregiver can be provided with the container 202 by a physician, pharmacist, etc.

A timing schedule 204 is provided inside the container indicating when each of the pills 100 of the kit 200 is to be taken, e.g., the time and day of the week. The timing schedule 204 includes an area 206 where a physician, pharmacist, etc. can write the time when the pills 100 for each particular day are to be taken, and circle am or pm. Two or more pills 100 may need to be taken at a particular time of a given day, as shown by FIG. 4, where each pill has a different medicament stored therein and a different preset dispensing timing pattern. As such, an individual can take all of the pills 100 which are indicated to be taken at the particular time of the given day and not take any other pills 100 until the same time the following day.

Since each of the pills 100 of the kit 200 has a programmed preset dispensing timing pattern, there is little or no concern that the medicaments from each pill 100 would interact with each other even though the pills 100 are taken at the same time. For example, one of the pills 100 of the kit 200 can start dispensing immediately, while another pill 100 of the kit 200 would not start dispensing until three hours later.

Figure 5:
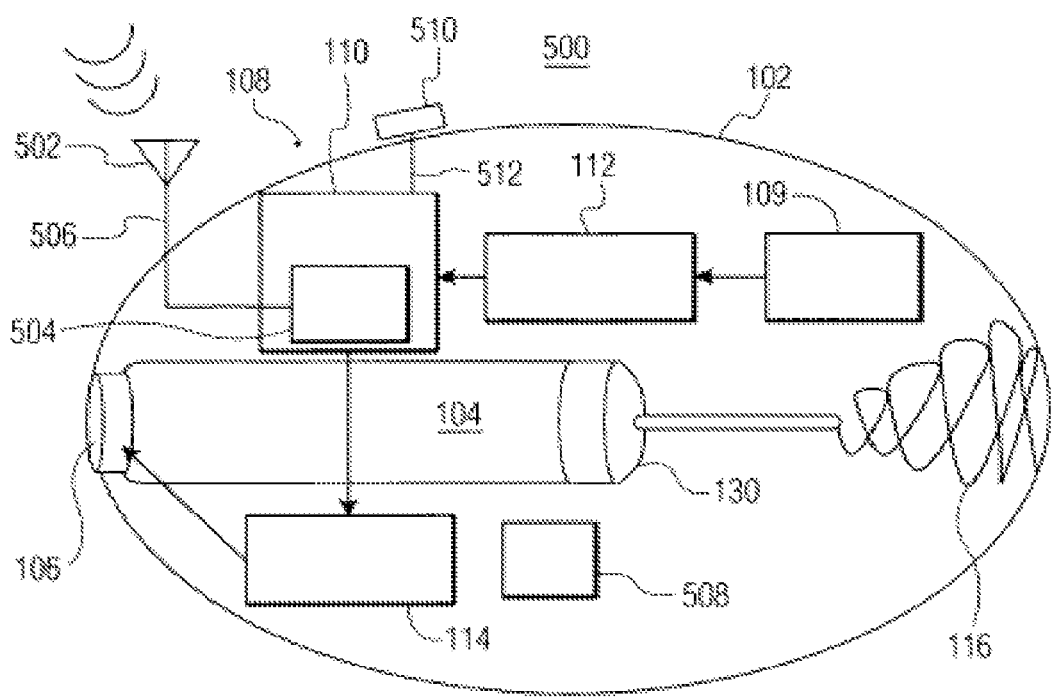
FIG. 5 is a schematic diagram of a remote-controlled pill in accordance with a first embodiment of the present invention.
Figure 6:
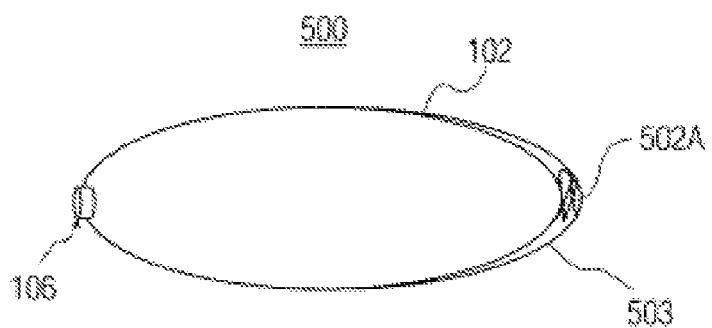
FIG. 6 is a schematic diagram of a remote-controlled pill in accordance with a second embodiment of the present invention.

In an alternate embodiment of the pill 100, as shown by FIG. 5, and designated generally by reference numeral 500, the remote-controlled pill 500 is provided with an antenna 502 for receiving control signals, such as RF control signals, for remotely communicating commands or instructions to the pill 500 for controlling the pill 500. The antenna 502 may also transmit information from the pill 500 to the outside as further described below. In an alternative embodiment, as shown by FIG. 6, an antenna 502A can be provided in a folded configuration and encapsulated by a soluble membrane 503. When the pill 500 is ingested, the soluble membrane 503 is dissolved, which then allows the antenna 502A to unfold.

The pill 500 operates substantially in the same manner as the pill 100, except for the operational differences described below with respect to the former pill's remote-control capabilities. The pill 500 includes the same components as the pill 100 where identical reference numbers in FIGS. 1 and 5 identify similar components. A plurality of pills 500 can be packaged as a kit as described above with reference to FIG. 4.

The control signals received by the pill 500 are transmitted to RF communication circuitry 504 within the timing circuitry 110 via wire leads 506. The RF communication circuitry 504 includes a receiver and processing circuitry for processing and analyzing the received RF control signals and accordingly determining one or more particular actions indicative of the instructions or codes provided by the control signals. The actions are determined by correlating the instructions or codes with one or more actions using a data structure, such as look-up table, within the timing circuitry 110.

The instructions provided by the control signals can include overriding the preset dispensing timing pattern programmed within the timing circuitry 110 for one or more moments in time during the dispensing time period. This may be necessary to dynamically increase or decrease the amount of medicament being dispensed during a particular time during the dispensing time period due to the person's vitals at a particular moment in time and other factors. The person's vitals can be monitored using conventional systems and sensors. One or more of these sensors can be provided within the pill 500 itself for sensing the person's vitals as the pill 500 traverses the gastrointestinal tract and for transmitting the information to the timing circuitry 110 which in turn dynamically adjusts the dosage based on the person's sensed vitals.

The instructions provided by the control signals can further change the dispensing timing pattern by reprogramming the timing circuitry 110 with a different dispensing timing pattern. The control signals can further provide instructions as to which moment in time of the new dispensing timing pattern the dispensing of the medicament should commence. The new dispensing timing pattern can be transmitted via the control signals or be stored within a memory of the timing circuitry 110, where the memory includes a plurality of dispensing timing patterns and the control signals indicate which dispensing timing pattern is desired.

Figure 7:
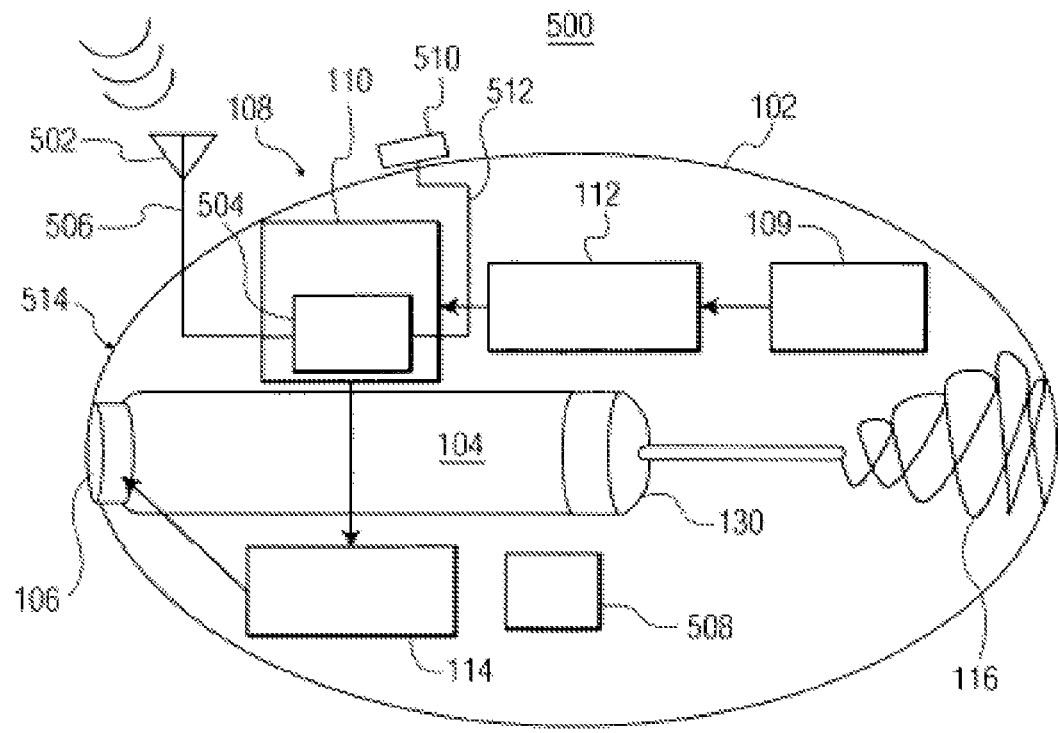
FIG. 7 is a schematic diagram of a remote-controlled pill in accordance with a third embodiment of the present invention.

The control signals can also instruct the control and timing circuitry 108 to terminate the dispensing of the medicament within the body, in case the wrong medicament was administered, the wrong dose was prescribed, the person had an adverse reaction to the medicament, etc. The control signals can further instruct the control and timing circuitry 108 to release a bowel slowing medication, such as Lomotil®, stored within a reservoir or micro-sac 514 (FIG. 7) of the pill 500 for temporarily halting the progress of the pill 500 through the gastrointestinal tract. The bowel slowing medications can be released in tandem with the medicament stored within the reservoir 104. The bowel slowing medication can also be provided within a separate pill.

The generation and transmission of the control signals can be synchronized with an external system, such as an MRI system, ultrasound imaging system, etc., for dispensing the medicament in accordance with the person's vitals monitored by the external system, the mode of operation of the external systems, etc. The medicament can be an oral contrast agent used to enhance diagnostic images. An example of such a contrast agent is Gastromark® for MRI images and Barium for CT images.

In addition to releasing contrast agents for each modality, the release time can be used for diagnostic purposes. A common problem in multi-modal imaging (e.g. any combination of CT, PET, MRI, Ultrasound, X-Ray, etc.) is the registration of images. Between images, patient motion causes difficulties in 'registering' different images to one another. Patient motion includes walking between the exams as well as voluntary and involuntary internal motions such as breathing, heart beating, and digestion.

The pill 500 can be used to release contrast agents in particular areas that can be estimated by time in order to minimize the contrast agent required or concentrate it in a particular area. Use of contrast agent does not only register the images in terms of location, but in terms of time. This fourth dimension can improve the accuracy of co-registration.

The controlled timing of contrast agents can also be used diagnostically to measure the timing through different parts of the GI tract. This demonstrates the effectiveness of peristaltic action (the movement of muscles that propel food through the GI tract). Locating failed areas of peristaltic action can aid the diagnosis of diseases, such as Crohn's disease and other obstructive bowel problems.

The control signals preferably transmit unique identification information which is used by the timing circuitry 110 to ensure that the received control signals are for the respective pill 500. This prevents control signals from initiating an action to a pill 500 other than the intended pill 500. The identification information can be a unique serial number which is programmed within the timing circuitry 110. If the received serial number does not match the programmed serial number, the timing circuitry 110 does not respond to the received control signals. Accordingly, the timing circuitry 110 does not perform any action, such as the actions described above.

The communication circuitry 504 includes a transmitter for transmitting signals from the pill 500. The signals are generated by the communication circuitry 504 for providing information to a caregiver or the person. Information that can be provided includes the particular moment in time of the dispensing time period; the cumulative quantity of medicament dispensed from the beginning of the dispensing time period to a particular moment in time of the dispensing time period; the average quantity of medicament dispensed during each moment in time of the dispensing time period (e.g., each second); etc.

Additionally, the transmitter can provide a signal for alerting or notifying a caregiver or the person that the pill 500 has been taken, in case the caregiver or the person do not remember if the pill 500 was or was not taken. The transmitter can also provide a signal if the pill 500 after diagnostic tests are executed by the control and timing circuitry 108 and it is determined that the pill 500 has malfunctioned, in cases such as if the pill 500 is not dispensing the medicament, the medicament is not being dispensed according to the preset dispensing timing pattern, etc.

The pill 500 includes an optional RFID tag 508 for tracking, identification, inventory and other purposes using an RFID reading system. The RFID tag 508 can also be used to determine if the pill 500 was administered by a caregiver or taken by the person, and if so, the RFID tag 508 can be used to determine the general location of the pill 500 within the gastrointestinal tract.

The pill 500 further includes a piezo-electric element and associated circuitry 510 for remotely transmitting commands via the communication circuitry 504 to the timing circuitry 110 for remotely controlling the pill 500. The element 510 is preferably affixed to the housing 102 and is capable of being vibrated at one or more predetermined frequencies. The vibration is caused by placing an ultrasound probe, hydrophone or other vibration-causing device in proximity to the person.

The frequencies caused by the element 510 are converted to electrical signals by the associated circuitry. The electrical signals are transmitted to the timing circuitry 110 via wire lead 512 where they are processed for determining an action to perform. The action can be one of the actions described above with reference to the control signals provided to the timing circuitry 110 via the wire leads 506. The action is preferably determined by correlating the vibration of the element 510 to an action using a data structure, such as a look-up table, stored within the control and timing circuitry 108 and accessible by the timing circuitry 110.

Figure 8:
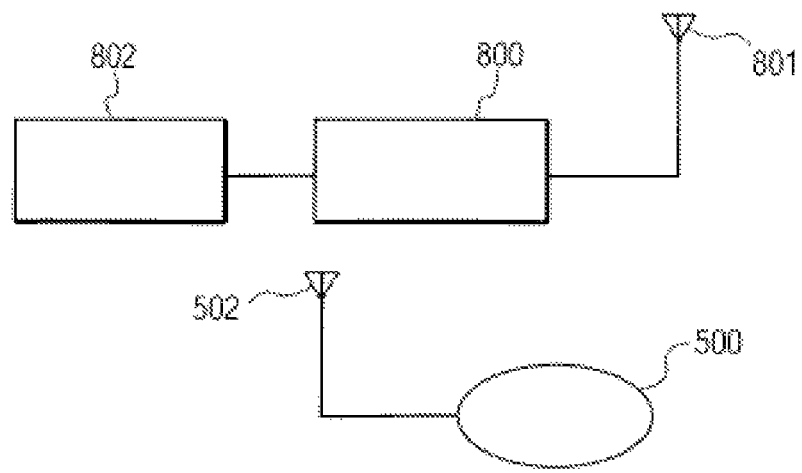
FIG. 8 is a block diagram of a dose managing system for controlling dispensing of a medicament by a remote-controlled pill in accordance with the present invention.

With reference to FIG. 8, the communication circuitry 504 of the remote-controlled pill 500 is able to communicate with a transmitter/receiver 800 via antenna 502 (or piezo electric equivalent 510) of a dosage management system 900. The transmitter/receiver 800 forwards commands determined by a Dose Manager 802 via an antenna 801. The Dose Manager 802 is a computing device, such as a personal computer, which may be connected to the Internet or other network, such as a LAN. The Dose Manager 802 receives patient vital sign information electronically from advanced monitoring systems and/or biosensor devices including pulse, oxygen level from a pulse-oximeter, EKG, blood pressure, blood protein level, body temperature, body fluid composition; and/or from a manual computer entry, such as from a keyboard. Based on the received information, the dosage of the medicament is adjusted as described below.

The biosensor devices may include electrodes positioned on the user. One or more biosensor devices can be included within the pill 500 itself. The patient or doctor may also enter auxiliary information into the Dose Manager 802, such as the degree or level of pain, which typically cannot be measured directly.

The information received by the Dose Manager 802 is used by the control and timing circuitry 110 to automatically control the desired dosage or the quantity of medicament to be dispensed by the remote-controlled pill 500. External or non-measured information can also be used to direct the desired dosage. For example, a barometric reading, and weather reported or anticipated (snow, rain, etc.) for a particular zip code (such as is available on www.weather.com) may drive the amount of arthritis medication delivered by the remote-controlled pill 500. Similarly, pollen counts and other allergens are often available via the Internet for particular areas. Allergy medication can be dispensed as a function of the particular allergen sensitivity of the patient. For more accurate and automatic control, a GPS located on the patient can send information to the Dose Manager 802 to determine the current location and zip code of the patient. Wireless communication, such as by cell phone can alternatively substitute for the Internet or communication between the GPS and Dose Manager 802.

Information derived from a patient's electronic calendar or schedule stored in a PDA, or alarm clock can also be used to infer proper dosing. For example, an early appointment may trigger earlier release of arthritis medication, enabling the patient to wake and become more productive as a function of the demands of the day.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. A medicament delivery system for dispensing a medicament to a gastrointestinal tract of a body, said system comprising:
   a housing;
   an opening in the housing;
   a reservoir for storing said medicament within said housing, the reservoir being in fluid communication with the opening;
   a pressure mechanism disposed in the housing for applying pressure to the reservoir to direct the medicament toward the opening;
   control and timing circuitry programmed with a dispensing timing pattern and comprising a clock, wherein the timing circuitry is adapted to transmit a release signal according to the timing pattern and the clock independent of a sensed physiological parameter of the gastrointestinal tract and independent of a contemporaneous signal from outside the body; and
   a release controller for receiving the release signal and controlling a release of the medicament from the reservoir.

2. The system according to claim 1, further comprising at least one antenna and RF communication circuitry for receiving RF control signals to perform an action selected from the group consisting of reprogramming the control and timing circuitry with another dispensing timing pattern, terminating the dispensing of said medicament, dispensing another medicament, changing the dispensing timing pattern, and dispensing said medicament according to a person's vitals.

3. The system according to claim 2, further comprising a soluble membrane encapsulating said at least one antenna.

4. The system according to claim 1, further comprising a piezo-electric element capable of being vibrated at at least one predetermined frequency.

5. The system according to claim 4, further comprising a data structure for correlating said at least one predetermined frequency with an action, and wherein said action is selected from the group consisting of reprogramming the control and timing circuitry with another dispensing timing pattern, terminating the dispensing of said medicament, dispensing another medicament, changing the dispensing timing pattern, and dispensing said medicament according to a person's vitals.

6. The system according to claim 1, further comprising a transmitter.

7. The system according to claim 1, further comprising an RFID tag.

8. The system according to claim 1, wherein said control and timing circuitry comprises a start timer mechanism wherein said start timer mechanism transmits a signal to said timing circuitry for clocking a dispensing time period, and wherein said timing circuitry transmits a signal to said release controller for dispensing said medicament substantially according to said dispensing timing pattern during said dispensing time period.

9. The system according to claim 1, wherein said dispensing timing pattern correlates an approximate quantity of said medicament to be dispensed during each moment of time during a dispensing time period.

10. The system according to claim 1, further comprising another reservoir for storing another medicament.

11. The system according to claim 1, further comprising a dosage management system for relaying commands to said control and timing circuitry for controlling the dispensing of said medicament in accordance with pre-obtained information selected from the group consisting of weather information, barometric reading, pollen count information and patient-related information.

12. The system according to claim 1, further comprising communication means for communicating with an imaging system, wherein said medicament is dispensed in synchronization with said imaging system.

13. The system of claim 1, further comprising a check valve disposed in the opening.

14. The system of claim 1, wherein the pressure mechanism is a spring.

15. The system of claim 1, wherein the reservoir comprises a micro-syringe comprising a plunger and the pressure mechanism applies a pressure to the plunger.

16. A medicament treatment kit comprising:
   a container enclosing a plurality of medicament delivery systems for delivering a medicament to a body, while traversing a gastrointestinal tract of the body, wherein each system comprises:
   a housing having an opening disposed therein;
   a reservoir for storing said medicament within said housing and in fluid communication with the opening;
   a pressure mechanism disposed in the housing for applying pressure to the reservoir to direct the medicament toward the opening;
   control and timing circuitry programmed with a dispensing timing pattern and comprising a clock, wherein the timing circuitry is adapted to transmit a release signal according to the timing pattern and the clock independent of a sensed physiological parameter of the gastrointestinal tract and independent of a contemporaneous signal from outside the body;
   a release controller for receiving the release signal and controlling a release of the medicament from the reservoir; and
   a schedule indicating when each of the medicament delivery systems is to be taken.

17. The kit according to claim 16, further comprising at least one antenna and RF communication circuitry for receiving RF control signals instructing said system to perform an action, and wherein said action is selected from the group consisting of reprogramming the control and timing circuitry with another dispensing timing pattern, terminating the dispensing of said medicament, dispensing another medicament, changing the dispensing timing pattern, and dispensing said medicament according to a person's vitals.

18. The kit according to claim 17, further comprising a soluble membrane encapsulating said at least one antenna.

19. The kit according to claim 16, further comprising a piezo-electric element capable of being vibrated at at least one predetermined frequency.

20. The kit according to claim 19, further comprising a data structure for correlating said at least one predetermined frequency with an action, and wherein said action is selected from the group consisting of reprogramming the control and timing circuitry with another dispensing timing pattern, terminating the dispensing of said medicament, dispensing another medicament, changing the dispensing timing pattern, and dispensing said medicament according to a person's vitals.

21. The kit according to claim 16, wherein each system further comprises an RFID tag.

22. The kit according to claim 16, wherein said control and timing circuitry comprises a start timer mechanism, wherein said start timer mechanism transmits a signal to said timing circuitry for clocking a dispensing time period, and wherein said timing circuitry transmits a signal to said release controller for dispensing said medicament substantially according to said dispensing timing pattern during said dispensing time period.

23. The kit according to claim 16, wherein said dispensing timing pattern correlates an approximate quantity of said medicament to be dispensed during each moment of time during a dispensing time period.

24. The kit according to claim 16, further comprising another reservoir for storing another medicament.

25. The kit of claim 16, further comprising a check valve disposed in the opening.

26. The kit of claim 16, wherein the pressure mechanism is a spring.

27. The kit of claim 16, wherein the reservoir comprises a micro-syringe comprising a plunger and the pressure mechanism applies a pressure to the plunger.

* * * * *